US007067650B1

United States Patent
Tanaka

(10) Patent No.: US 7,067,650 B1
(45) Date of Patent: Jun. 27, 2006

(54) RIBOZYMES TARGETING BRADEION TRANSCRIPTS AND USE THEREOF

(75) Inventor: Manami Tanaka, Tsukuba (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 742 days.

(21) Appl. No.: 09/718,098

(22) Filed: Nov. 22, 2000

(51) Int. Cl.
C07H 21/04 (2006.01)

(52) U.S. Cl. .................. 536/24.5; 536/23.1; 536/24.31; 536/24.33

(58) Field of Classification Search .................. 514/44; 536/24.5, 23.1, 24.3, 24.33; 435/325, 375, 435/6, 91.1
See application file for complete search history.

(56) References Cited

U.S. PATENT DOCUMENTS

| | | | | |
|---|---|---|---|---|
| 5,871,973 A | * | 2/1999 | Hillman et al. | ............ 435/69.1 |
| 5,928,899 A | | 7/1999 | Hillman et al. | |
| 6,423,504 B1 | * | 7/2002 | Tanaka et al. | ............ 435/7.23 |

OTHER PUBLICATIONS

Gura, T. Systems for Identifying New Drugs are Often Faulty. Science, 1997 vol. 278:1041–1042.*
Sokol et al. Antisense and ribozyme constructs in transgenic animals. Transgenic Research, 1996 vol. 5:363–371.*
Burke, JM. Hairpin ribozyme: Current status and future prospects. Biochem Soc Trans., 1996 vol. 24:608–615.*
Branch, A. A Good Antisense is Hard to Find. TIBS, Feb. 1998 vol. 23, pp. 45–50.*
Jen et al. Suppression of Gene Expression by Targeted Disruption of Messenger RNA: Available Options and Current Strategies. Stem Cells, 2000, vol. 18:307–319.*
Dias et al. Potential roles of antisense oligonucleotides in cancer therapy. The example of bcl-2 antisense oligonucleotides. European Journal of Pharmaceutics and Biopharmaceutics, 2002 vol. 54:263–269.*
Tanabe et al. Maxizymes, Novel Allosterically Controllable Ribozymes, Can be Designed to Cleave Various Substrates. Biomacromolecules, 2000; vol. 1:108–117.*
Tanaka et al. 22nd Annual Meeting of Japan Molecular Biology Society Programs and Abstracts; Dec. 7–10, 1999.*
$22^{nd}$ Annual Meeting of Japan Molecular Biology Society Programs and Abstracts; Dec. 7–10, 1999; Issued Nov. 22, 1999; Sponsored by the organizing Committee for Annual Meeting of Japan Molecular Biology Society.

* cited by examiner

Primary Examiner—Sean McGarry
Assistant Examiner—Terra C. Gibbs
(74) Attorney, Agent, or Firm—Foley & Lardner LLP

(57) ABSTRACT

This invention relates to: a set of ribozymes which comprises at least one ribozyme capable of binding and cleaving Bradeion α mRNA which corresponds to DNA comprising a nucleotide sequence shown in SEQ ID NO:1, and at least one ribozyme capable of binding to and cleaving Bradeion β mRNA which corresponds to DNA comprising a nucleotide sequence shown in SEQ ID NO:3; a set of vectors comprising ribozymes; a pharmaceutical composition comprising set of vectors; and a method for treating a subject with a cancer using set of vectors.

12 Claims, 5 Drawing Sheets

Bradeion α

| | |
|---|---|
| MDRSLGWQGNSVPEDRTEAGIKRFLEDTTDDGELSKFVKDFSGNASCHPPEAKTWASRPQVPEPRPQAPDLYDDDLEFRPPSRPQSSDNQQYFCAPAPLS | 100 |
| PSARPRSPWGKLDPYDSSEVEPPALPLPFSGLLQEDRGQGAECVCVCVCVCVCLCVCVSGTYFSPVSALAPRYLPPRALSICSFSKGRRPSWWPQMGT | 200 |
| HRSLALLF        transmembrane region | 208 |

Bradeion β

| | |
|---|---|
| MDRSLGWQGNSVPEDRTEAGIKRFLEDTTDDGELSKFVKDFSGNASCHPPEAKTWASRPQVPEPRPQAPDLYDDDLEFRPPSRPQSSDNQQYFCAPAPLS | 100 |
| PSARPRSPWGKLDPYDSSEDKEYVGFATLPWQVERKSVKKGFDFTLMVAGESGLGKSTLVNSLFLTDLYRDRKLLGAEERIMQTVEITKHAVDIEEKGV | 200 |
| ATG/GTP-binding site motif A (P-loop) | |
| RLRLTIVDTPGFGDAVKNTECWKPVAEYIDQQFEQYFRDESGLNRKNIQDNRVHCCLYFISPFGHGLRPLDVEFMKALBQRVNIVPILAKADTLTPPEVD | 300 |
| HKKRKIRHEIEHFGIKIYQFPDCDSDEDEDFKLQDQALKESIPFAVIGSNTVVEARGRRVRGRLYPWGIVEVENPGHCDFVKLRTMLVRTHMQDLKDVTR | 400 |
| ETHYEMYRAQCIQSMTRLVVKERMRNKLTRESGTDFPIPAVPPGTDPETEKLIREKDEELRRMQEMLHKIQKQMKEHY | 478 |

* * *

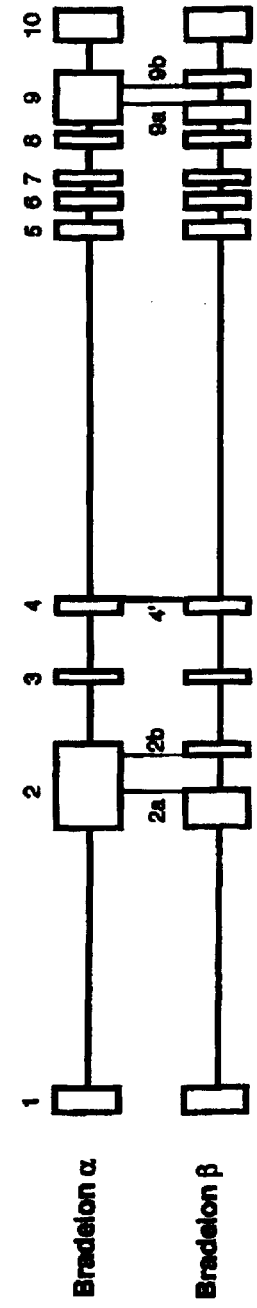

FIG. 3

| Case No. | Age/sex | Hist. type | Dukes' stage | K-ras (codon 12) | Bradeion RT-PCR | In situ hybridization |
|---|---|---|---|---|---|---|
| T1 | 81/M | Ad (mod) | A | - | ND | + |
| T2 | 51/F | Ad (mod) | B | - | ND | + |
| T3 | 71/M | Ad (mod) | C | - | +* | + |
| T4 | 70/M | Ad (mod) | C | - | ND | + |
| T5 | 40/M | Ad (mod) | C | - | ND | + |
| T6 | 75/M | Ad (well) | A | - | ND | + |
| T7 | 71/F | Ad (well) | B | GTT | +* | + |
| T8 | 56/M | Ad (well) | B | - | ND | + |
| T9 | 70/F | Ad (well) | C | GGT | +* | + |
| T10 | 54/M | Ad (well) | C | GAT | ND | + |
| T11 | 73/F | MM | A | - | ND | + |
| T12 | 63/M | Muc | A | - | +* | + |
| T13 | 68/F | Muc | C | GAT | +* | + |
| N1 | 54/M | normal | - | - | - | - |
| N2 | 81/M | normal | - | - | - | - |

SEQUENCE LISTING

<160> NUMBER OF SEQ ID NOS: 23

<210> SEQ ID NO 1
<211> LENGTH: 2220
<212> TYPE: DNA
<213> ORGANISM: Homo sapiens

<400> SEQUENCE: 1

| | | | | | |
|---|---|---|---|---|---|
| agcatcaaaa | caaggctgtt | tctgtgtgtg | aggaactttg | cctgggagat | aaaattagac | 60 |
| ctagagcttt | ctgacaggga | gtctgaagcg | tgggacatgg | accgttcact | gggatggcaa | 120 |
| gggaattctg | tccctgagga | caggactgaa | gctgggatca | agcgtttcct | ggaggacacc | 180 |
| acggatgatg | gagaactgag | caagttcgtg | aaggatttct | caggaaatgc | gagctgccac | 240 |
| ccaccagagg | ctaagacctg | gcatccagg | ccccaagtcc | cggagccaag | gccccaggcc | 300 |
| ccggacctct | atgatgatga | cctggagttc | agaccccct | cgcggcccca | gtcctctgac | 360 |
| aaccagcagt | acttctgtgc | ccagccccct | ctcagcccat | ctgccaggcc | ccgcagccca | 420 |
| tggggcaagc | ttgatcccta | tgattcctct | gaggtagagc | ctccagccct | gcctttgcct | 480 |
| ttcagtgggc | tgctgcagga | agaccggggg | cagggagcag | agtgtgtgtg | tgtgtgtgtg | 540 |
| tgtgtgtgtg | tgtgtgtgtg | tttgtgtgtg | tgtgtatctg | ggacctattt | cagtcctgtg | 600 |
| tcagccctag | ctccaagata | tctgccccca | agggcactgg | aaatttgcag | tttcagcaag | 660 |
| ggcaggaggc | ccctcggtg | gcctcagatg | ggaactcaca | gaagtctggc | actgcttttt | 720 |
| taaggctggg | gcaaaggcct | gaaagggaga | gaagattggc | gctgggtgcc | ggggcccctt | 780 |
| tggctcctca | ccgtgatgca | ttctgccttc | ctgtctacta | ggatgacaag | gagtatgtgg | 840 |
| gctttgcaac | cctccccaac | caagtccacc | gaaagtccgt | gaagaaaggc | tttgacttta | 900 |
| ccctcatggt | ggcaggagag | tctggcctgg | gcaaatccac | acttgtcaat | agcctcttcc | 960 |
| tcactgatct | gtaccgggac | cggaaacttc | ttggtgctga | agagaggatc | atgcaaactg | 1020 |
| tggagatcac | taagcatgca | gtggacatag | aagagaaggg | tgtgaggctg | cggctcacca | 1080 |
| ttgtggacac | accaggtttt | ggggatgcag | tcaacaacac | agagtgctgg | aagcctgtgg | 1140 |
| cagaatacat | tgatcagcag | tttgagcagt | atttccgaga | cgagagtggc | ctgaaccgaa | 1200 |
| agaacatcca | agacaacagg | gtgcactgct | gcctgtactt | catctcaccc | ttcggccatg | 1260 |
| ggctccggcc | attggatgtt | gaattcatga | aggccctgca | tcagcgggtc | aacatcgtgc | 1320 |
| ctatcctggc | taaggcagac | acactgacac | tcccgaagt | ggaccacaag | aaacgcaaaa | 1380 |
| tccgggagga | gattgagcat | tttggaatca | agatctatca | attcccagac | tgtgactctg | 1440 |
| atgaggatga | ggacttcaaa | ttgcaggacc | aagccctaaa | ggaaagcatc | ccatttgcag | 1500 |
| taattggcag | caacactgta | gtagaggcca | gagggcggcg | agttcggggt | cgactctacc | 1560 |
| cctggggcat | cgtggaagtg | gaaaacccag | ggcactgcga | ctttgtgaag | ctgaggacaa | 1620 |

-continued

```
tgctggtacg tacccacatg caggacctga aggatgtgac acgggagaca cattatgaga      1680
actaccgggc acagtgcatc cagagcatga cccgcctggt ggtgaaggaa cggaatcgca      1740
agtatgacca gaagccagga caaagctggc aggggagat cccaagccta gccttgggtg       1800
agaccaagcc ctactttgt tcttctatag gccctgggct caatctaagc gggtgctggg       1860
gtcctcctcg ccttatcaac cctttctcc ctttagcaaa ctgactcggg aaagtggtac       1920
cgacttcccc atccctgctg tcccaccagg acagatcca gaaactgaga agcttatccg       1980
agagaaagat gaggagctgc ggcggatgca ggagatgcta cacaaaatac aaaaacagat      2040
gaaggagaac tattaactgg cttcagccc tggatattta aatctcctcc tcttcttcct      2100
gtccatgccg cccctccca gcaccagctc tgctcaggcc ccttcagcta ctgccacttc       2160
gccttacatc cctgctgact gcccagagac tcagaggaaa taaagtttaa taaatctgta     2220
```

<210> SEQ ID NO 2
<211> LENGTH: 208
<212> TYPE: PRT
<213> ORGANISM: Homo sapiens

<400> SEQUENCE: 2

```
Met Asp Arg Ser Leu Gly Trp Gln Gly Asn Ser Val Pro Glu Asp Arg
  1               5                  10                  15

Thr Glu Ala Gly Ile Lys Arg Phe Leu Glu Asp Thr Thr Asp Asp Gly
             20                  25                  30

Glu Leu Ser Lys Phe Val Lys Asp Phe Ser Gly Asn Ala Ser Cys His
         35                  40                  45

Pro Pro Glu Ala Lys Thr Trp Ala Ser Arg Pro Gln Val Pro Glu Pro
     50                  55                  60

Arg Pro Gln Ala Pro Asp Leu Tyr Asp Asp Leu Glu Phe Arg Pro
 65                  70                  75                  80

Pro Ser Arg Pro Gln Ser Ser Asp Asn Gln Gln Tyr Phe Cys Ala Pro
                 85                  90                  95

Ala Pro Leu Ser Pro Ser Ala Arg Pro Arg Ser Pro Trp Gly Lys Leu
            100                 105                 110

Asp Pro Tyr Asp Ser Ser Glu Val Glu Pro Ala Leu Pro Leu Pro
        115                 120                 125

Phe Ser Gly Leu Leu Gln Glu Asp Arg Gly Gln Gly Ala Glu Cys Val
    130                 135                 140

Cys Val Cys Val Cys Val Cys Val Cys Leu Cys Val Cys Val
145                 150                 155                 160

Ser Gly Thr Tyr Phe Ser Pro Val Ser Ala Leu Ala Pro Arg Tyr Leu
                165                 170                 175

Pro Pro Arg Ala Leu Glu Ile Cys Ser Phe Ser Lys Gly Arg Arg Pro
            180                 185                 190

Ser Trp Trp Pro Gln Met Gly Thr His Arg Ser Leu Ala Leu Leu Phe
        195                 200                 205
```

<210> SEQ ID NO 3
<211> LENGTH: 1735
<212> TYPE: DNA
<213> ORGANISM: Homo sapiens

<400> SEQUENCE: 3

```
gaaaggagca agccaggaag ccagacaaca acagcatcaa acaaggctg tttctgtgtg        60 tgaggaactt tgcctgggag ataaaattag acctagagct ttctgacagg gagtctgaag      120
```

-continued

```
cgtgggacat ggaccgttca ctgggatggc aagggaattc tgtccctgag gacaggactg      180
aagctgggat caagcgtttc ctggaggaca ccacggatga tggagaactg agcaagttcg      240
tgaaggattt ctcaggaaat gcgagctgcc acccaccaga ggctaagacc tgggcatcca      300
ggccccaagt cccggagcca aggccccagg ccccggacct ctatgatgat gacctggagt      360
tcagaccccc ctcgcggccc cagtcctctg acaaccagca gtacttctgt gccccagccc      420
ctctcagccc atctgccagg ccccgcagcc catgggcaa gcttgatccc tatgattcct       480
ctgaggatga caaggagtat gtgggctttg caaccctccc caaccaagtc caccgaaagt      540
ccgtgaagaa aggctttgac tttaccctca tggtggcagg agagtctggc ctgggcaaat      600
ccacacttgt caatagcctc ttcctcactg atctgtaccg ggaccggaaa cttcttggtg      660
ctgaagagag gatcatgcaa actgtggaga tcactaagca tgcagtggac atagaagaga      720
agggtgtgag gctgcggctc accattgtgg acaccagg ttttggggat gcagtcaaca        780
acacagagtg ctggaagcct gtggcagaat acattgatca gcagtttgag cagtatttcc      840
gagacgagag tggcctgaac cgaaagaaca tccaagacaa cagggtgcac tgctgcctgt      900
acttcatctc acccttcggc catgggctcc ggccattgga tgttgaattc atgaaggccc      960
tgcatcagcg ggtcaacatc gtgcctatcc tggctaaggc agacacactg cacctcccg     1020
aagtggacca caagaaacgc aaaatccggg aggagattga gcattttgga atcaagatct     1080
atcaattccc agactgtgac tctgatgagg atgaggactt caaattgcag gaccaagccc     1140
taaaggaaag catcccattt gcagtaattg cagcaacac tgtagtagag gccagagggc      1200
ggcgagttcg gggtcgactc tacccctggg gcatcgtgga agtggaaaac ccagggcact     1260
gcgactttgt gaagctgagg acaatgctgg tacgtaccca catgcaggac ctgaaggatg     1320
tgacacggga gacacattat gagaactacc gggcacagtg catccagagc atgacccgcc     1380
tggtggtgaa ggaacggaat cgcaacaaac tgactcggga agtggtacc gacttcccca      1440
tccctgctgt cccaccaggg acagatccag aaactgagaa gcttatccga gagaaagatg     1500
aggagctgcg gcggatgcag gagatgctac acaaaataca aaaacagatg aaggagaact     1560
attaactggc tttcagccct ggatatttaa atctcctcct cttcttcctg tccatgccgg     1620
cccctcccag caccagctct gctcaggccc cttcagctac tgccacttcg cctaacatcc     1680
ctgctgactg cccagagact cagaggaaat aaagtttaat aaatctgtag gtggc          1735
```

<210> SEQ ID NO 4
<211> LENGTH: 478
<212> TYPE: PRT
<213> ORGANISM: Homo sapiens

<400> SEQUENCE: 4

```
Met Asp Arg Ser Leu Gly Trp Gln Gly Asn Ser Val Pro Glu Asp Arg
 1               5                  10                  15

Thr Glu Ala Gly Ile Lys Arg Phe Leu Glu Asp Thr Thr Asp Asp Gly
            20                  25                  30

Glu Leu Ser Lys Phe Val Lys Asp Phe Ser Gly Asn Ala Ser Cys His
        35                  40                  45

Pro Pro Glu Ala Lys Thr Trp Ala Ser Arg Pro Gln Val Pro Glu Pro
    50                  55                  60

Arg Pro Gln Ala Pro Asp Leu Tyr Asp Asp Leu Glu Phe Arg Pro
65                  70                  75                  80

Pro Ser Arg Pro Gln Ser Ser Asp Asn Gln Gln Tyr Phe Cys Ala Pro
                85                  90                  95
```

-continued

```
Ala Pro Leu Ser Pro Ser Ala Arg Pro Arg Ser Pro Trp Gly Lys Leu
            100                 105                 110

Asp Pro Tyr Asp Ser Ser Glu Asp Asp Lys Glu Tyr Val Gly Phe Ala
            115                 120                 125

Thr Leu Pro Asn Gln Val His Arg Lys Ser Val Lys Lys Gly Phe Asp
            130                 135                 140

Phe Thr Leu Met Val Ala Gly Glu Ser Gly Leu Gly Lys Ser Thr Leu
145                 150                 155                 160

Val Asn Ser Leu Phe Leu Thr Asp Leu Tyr Arg Asp Arg Lys Leu Leu
                165                 170                 175

Gly Ala Glu Glu Arg Ile Met Gln Thr Val Glu Ile Thr Lys His Ala
            180                 185                 190

Val Asp Ile Glu Glu Lys Gly Val Arg Leu Arg Leu Thr Ile Val Asp
            195                 200                 205

Thr Pro Gly Phe Gly Asp Ala Val Asn Asn Thr Glu Cys Val Lys Pro
            210                 215                 220

Val Ala Glu Tyr Ile Asp Gln Gln Phe Glu Gln Tyr Phe Arg Asp Glu
225                 230                 235                 240

Ser Gly Leu Asn Arg Lys Asn Ile Gln Asp Asn Arg Val His Cys Cys
                245                 250                 255

Leu Tyr Phe Ile Ser Pro Phe Gly His Gly Leu Arg Pro Leu Asp Val
            260                 265                 270

Glu Phe Met Lys Ala Leu His Gln Arg Val Asn Ile Val Pro Ile Leu
            275                 280                 285

Ala Lys Ala Asp Thr Leu Thr Pro Pro Glu Val Asp His Lys Lys Arg
            290                 295                 300

Lys Ile Arg Glu Glu Ile Glu His Phe Gly Ile Lys Ile Tyr Gln Phe
305                 310                 315                 320

Pro Asp Cys Asp Ser Asp Glu Asp Glu Asp Phe Lys Leu Gln Asp Gln
                325                 330                 335

Ala Leu Lys Glu Ser Ile Pro Phe Ala Val Ile Gly Ser Asn Thr Val
            340                 345                 350

Val Glu Ala Arg Gly Arg Arg Val Arg Gly Arg Leu Tyr Pro Trp Gly
            355                 360                 365

Ile Val Glu Val Glu Asn Pro Gly His Cys Asp Phe Val Lys Leu Arg
            370                 375                 380

Thr Met Leu Val Arg Thr His Met Gln Asp Leu Lys Asp Val Thr Arg
385                 390                 395                 400

Glu Thr His Tyr Glu Asn Tyr Arg Ala Gln Cys Ile Gln Ser Met Thr
                405                 410                 415

Arg Leu Val Val Lys Glu Arg Asn Arg Asn Lys Leu Thr Arg Glu Ser
            420                 425                 430

Gly Thr Asp Phe Pro Ile Pro Ala Val Pro Pro Gly Thr Asp Pro Glu
            435                 440                 445

Thr Glu Lys Leu Ile Arg Glu Lys Asp Glu Glu Leu Arg Arg Met Asp
            450                 455                 460

Glu Met Leu His Lys Ile Gln Lys Gln Met Lys Glu Asn Tyr
465                 470                 475
```

<210> SEQ ID NO 5
<211> LENGTH: 35
<212> TYPE: RNA
<213> ORGANISM: Artificial Sequence
<220> FEATURE:

<223> OTHER INFORMATION: Description of Artificial Sequence: Ribozyme,
      Brad-alpha1

<400> SEQUENCE: 5
ucccagacug aggaccgaaa gguccgaaac acaca                              35

<210> SEQ ID NO 6
<211> LENGTH: 38
<212> TYPE: RNA
<213> ORGANISM: Artificial Sequence
<220> FEATURE:
<223> OTHER INFORMATION: Description of Artificial Sequence: Ribozyme,
      Brad-alpha2

<400> SEQUENCE: 6
gacacagcug augaggaccg aaagguccga aacugaaa                           38

<210> SEQ ID NO 7
<211> LENGTH: 38
<212> TYPE: RNA
<213> ORGANISM: Artificial Sequence
<220> FEATURE:
<223> OTHER INFORMATION: Description of Artificial Sequence: Ribozyme,
      Brad-alpha3

<400> SEQUENCE: 7
uagggcucug augaggaccg aaagguccga aacacagg                           38

<210> SEQ ID NO 8
<211> LENGTH: 38
<212> TYPE: RNA
<213> ORGANISM: Artificial Sequence
<220> FEATURE:
<223> OTHER INFORMATION: Description of Artificial Sequence: Ribozyme,
      Brad-alpha4

<400> SEQUENCE: 8
agugccacug augaggaccg aaagguccga aacuucug                           38

<210> SEQ ID NO 9
<211> LENGTH: 38
<212> TYPE: RNA
<213> ORGANISM: Artificial Sequence
<220> FEATURE:
<223> OTHER INFORMATION: Description of Artificial Sequence: Ribozyme,
      Brad-beta1

<400> SEQUENCE: 9
cgcuucacug augaggaccg aaagguccga aacucccu                           38

<210> SEQ ID NO 10
<211> LENGTH: 38
<212> TYPE: RNA
<213> ORGANISM: Artificial Sequence
<220> FEATURE:
<223> OTHER INFORMATION: Description of Artificial Sequence: Ribozyme,
      Brad-beta2

<400> SEQUENCE: 10
ccucaggcug augaggaccg aaagguccga aacagaau                           38

<210> SEQ ID NO 11
<211> LENGTH: 38
<212> TYPE: RNA
<213> ORGANISM: Artificial Sequence
<220> FEATURE:

<223> OTHER INFORMATION: Description of Artificial Sequence: Ribozyme,
      Brad-beta3

<400> SEQUENCE: 11
gcuccggcug augaggaccg aaagguccga aacuuggg                              38

<210> SEQ ID NO 12
<211> LENGTH: 38
<212> TYPE: RNA
<213> ORGANISM: Artificial Sequence
<220> FEATURE:
<223> OTHER INFORMATION: Description of Artificial Sequence: Ribozyme,
      Brad-beta4

<400> SEQUENCE: 12
gucagagcug augaggaccg aaagguccga aacugggg                              38

<210> SEQ ID NO 13
<211> LENGTH: 27
<212> TYPE: RNA
<213> ORGANISM: Artificial Sequence
<220> FEATURE:
<223> OTHER INFORMATION: Description of Artificial Sequence: Ribozyme,
      Brad-beta3L

<400> SEQUENCE: 13
ggcuggaggc ucuaaucgaa acuuggg                                          27

<210> SEQ ID NO 14
<211> LENGTH: 30
<212> TYPE: RNA
<213> ORGANISM: Artificial Sequence
<220> FEATURE:
<223> OTHER INFORMATION: Description of Artificial Sequence: Ribozyme,
      Brad-beta3R

<400> SEQUENCE: 14
gcuccggcug augagagccu cagaggaauc                                       30

<210> SEQ ID NO 15
<211> LENGTH: 95
<212> TYPE: RNA
<213> ORGANISM: Artificial Sequence
<220> FEATURE:
<223> OTHER INFORMATION: Description of Artificial Sequence: tRNA(Val)
      promoter

<400> SEQUENCE: 15
accguugguu uccguagugu agugguuauc acguucgccu aacacgcgaa aggucccgg       60 uucgaaaccg ggcggaaaca aagacagucg cuuuu                                 95

<210> SEQ ID NO 16
<211> LENGTH: 91
<212> TYPE: DNA
<213> ORGANISM: Artificial Sequence
<220> FEATURE:
<223> OTHER INFORMATION: Description of Artificial Sequence: A mutant
      tRNA(Val) promoter

<400> SEQUENCE: 16
accgttggtt tccgtagtgt agtggttatc acgttcgcct aacacgcgaa aggtccccgg      60
ttcgaaaccg ggcactacaa aaaccaactt t                                     91

<210> SEQ ID NO 17
<211> LENGTH: 24

```
<212> TYPE: DNA
<213> ORGANISM: Artificial Sequence
<220> FEATURE:
<223> OTHER INFORMATION: Description of Artificial Sequence: Primer

<400> SEQUENCE: 17
ctgagcaagt tcgtgaagga tttc                                          24

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 18
cagtcctctg acaaccagca gta                                           23

<210> SEQ ID NO 19
<211> LENGTH: 15
<212> TYPE: RNA
<213> ORGANISM: Homo sapiens

<400> SEQUENCE: 19
uguguguauc uggga                                                    15

<210> SEQ ID NO 20
<211> LENGTH: 38
<212> TYPE: RNA
<213> ORGANISM: Homo sapiens

<400> SEQUENCE: 20
ucccagacug augaggaccg aaagguccga aacacaca                           38

<210> SEQ ID NO 21
<211> LENGTH: 15
<212> TYPE: RNA
<213> ORGANISM: Homo sapiens

<400> SEQUENCE: 21
cccaaguccc ggagc                                                    15

<210> SEQ ID NO 22
<211> LENGTH: 30
<212> TYPE: RNA
<213> ORGANISM: Homo sapiens

<400> SEQUENCE: 22
gcuccggcug augagagauc gaaacuuggg                                    30

<210> SEQ ID NO 23
<211> LENGTH: 27
<212> TYPE: RNA
<213> ORGANISM: Homo sapiens

<400> SEQUENCE: 23
ggcuggaggc ucuaccucag aggaauc                                       27
```

RIBOZYMES TARGETING BRADEION TRANSCRIPTS AND USE THEREOF

FIELD OF THE INVENTION

This invention relates to a set of antisense-ribozymes targeting bradeions α and β, to a set of vectors comprising said ribozymes, a pharmaceutical composition comprising said set of vectors, and a method for treating a subject with a cancer using said set of vectors.

BACKGROUND OF THE INVENTION

Cranial nerve cells (neurons) are main elements for controlling survival of higher order animals. Once the neurons are developed, they do not divide at all and only gradually exfoliate or go through necrosis. Exfoliation of the neurons occurs in the normal state but is particularly accelerated by genetic diseases, brain ischemia, or status epilepticus, or under conditions of poor nutrition and low oxygen. Some disorders of cranial nerves associated with aging (e.g., dementia) result from deficiency of an absolute amount of functional neurons caused by accumulation of exfoliated neurons. Thus, the monitoring and control of the exfoliation, as well as regeneration of the functions of neurons, are the most demanding subject to be solved among the aging problems.

Cranial nerve cells do not divide at all after the differentiation in the process of development, and maintain their functions or is accompanied by gradual deterioration of their functions throughout the life-time of the individual. They are presumed to have specific division-interrupting and function-maintaining mechanisms although these mechanisms have not yet been clarified. In the central nervous system, there exist numbers of unknown proteins and signaling substances, particularly stimulating substances and receptors thereof involved in brain-specific signal transduction, but many of their material basis still remains unknown.

Much research has been conducted worldwide on such an important element that controls the survival and maintenance of the cranial nerve cells. However, only a few elements were clarified in the substance or molecule level, and, prior to everything, it was necessary to develop techniques for discovery and analysis of those novel elements. Recently, the group of Dr. Masashi Yanagisawa and his colleagues of the University of Texas, Medical Research Center (authorized by the Howard Hughes Foundation) has succeeded in developing a technique for randomly screening neuropeptides and receptors thereof by using cultured cell and they have found a substance (named orexin) that directly binds to and stimulates the aperitive center in the hypothalamnus, and identified functions of the substance's receptor (Cell, 92, 573–585, 1998). However, such a systematic screening of substances is rare, and currently, stimulating factors involved in brain-specific signal transduction and receptors thereof are not yet fully clarified.

Under such circumstances, the present inventor and colleagues constructed an improved expressed complementary DNA (cDNA) library, developed a systematic screening technique, and succeeded in extraction and selection of genes specific for cranial nerve cells and found Bradeion α and β, whose expression occurs in brain, heart, and specific cancers only (U.S. application Ser. No. 09/440,936 filed Nov. 16, 1999). Bradeion β is also disclosed as a human cell division regulator in U.S. Pat. No. 5,871,973 and No. 5,928,899.

The object of this invention is to clarify the correlation between the presence of Bradeion α or β and specific cancers, and to utilize it for treatment of the cancers.

SUMMARY OF THE INVENTION

The present inventor has now found that when the bradeion transcripts (mRNAs) were cleaved with a set of bradeion α and β antisense-ribozymes, and this cleavage resulted in cell death and a specific inhibition of proliferation in cancers.

Thus, this invention, in one aspect thereof, provides a set of ribozymes which comprises at least one ribozyme capable of binding and cleaving Bradeion α mRNA which corresponds to DNA comprising a nucleotide sequence shown in SEQ ID NO:1, and at least one ribozyme capable of binding to and cleaving Bradeion β mRNA which corresponds to DNA comprising a nucleotide sequence shown in SEQ ID NO:3.

In an embodiment of this invention, said ribozyme capable of binding to and cleaving Bradeion α mRNA targets a sequence selected from the group consisting of RNA sequences corresponding to nucleotide numbers 569–583, 588–602, 595–609 and 699–713 of SEQ ID NO:1, and said ribozyme capable of binding and cleaving Bradeion β mRNA targets a sequence selected from the group consisting of RNA sequences corresponding to nucleotide numbers 108–122, 157–171, 304–318 and 378–392 of SEQ ID NO:3.

In another embodiment of this invention, each of said ribozymes is a hammerhead ribozyme. Said ribozymes may be a monomeric or heterodimeric ribozyme.

In further embodiment of this invention, said ribozymes are a combination of at least one ribozyme selected from the group consisting of ribozymes of SEQ ID NO:5, SEQ ID NO:6, SEQ ED NO:7 and SEQ ID NO:8, and at least one ribozyme selected from the group consisting of ribozymes of SEQ ID NO:9, SEQ ID NO:10, SEQ ID NO:11 and SEQ ID NO:12 and a heterodimeric ribozyme that is composed of an RNA sequence of SEQ ID NO:13 and an RNA sequence of SEQ ID NO:14. For example, said ribozymes may be a combination of a ribozyme of SEQ ID NO:7 and a ribozyme of SEQ 1D NO:9, 10 or 11; or a combination of a ribozyme of SEQ ID NO:8 and a ribozyme of SEQ ID NO:10 or 11.

This invention, in another aspect thereof, provides a vector comprising DNA that encodes a ribozyme as defined in claim 1 capable of binding and cleaving. Bradeion α mRNA which corresponds to DNA comprising a nucleotide sequence shown in SEQ ID NO: 1.

This invention, in further aspect thereof, provides a set of vectors which comprises: (i) a vector comprising DNA that encodes a ribozyme capable of binding and cleaving Bradeion α mRNA which corresponds to DNA comprising a nucleotide sequence shown in SEQ ID NO: 1; and (ii) a vector comprising DNA that encodes a ribozyme capable of binding and cleaving Bradeion β mRNA which corresponds to DNA comprising a nucleotide sequence shown in SEQ ID NO:3, wherein each of said DNA is operably linked to a promoter.

In an embodiment of this invention, said promoter is a polymerase III promoter. Specifically, said promoter is a tRNA promoter including tRNA$^{val}$ promoter or a variant thereof.

In further embodiment of this invention, each of said vectors comprise a terminator.

In further embodiment of this invention, each of said vectors is adenovirus or retrovirus.

This invention, in further aspect thereof, provides a pharmaceutical composition comprising a set of vectors of claim 9 in a therapeutically efficient amount.

In an embodiment of this invention, the pharmaceutical composition is for treatment of a cancer, including human colorectal cancer, human malignant melanoma, and human prostate cancer.

This invention, in one aspect thereof, provides a method for treating a subject with a cancer wherein said method comprises: introducing a set of vectors of claim 9 into cells in a cancerous tissue of the subject; and allowing said ribozymes to expressing within transformed or transfected cells in said tissue, thereby cleaving Bradeion α, Bradeion β, or the both in said cells.

In an embodiment of this invention, said cancer is human colorectal cancer or human malignant melanoma.

BRIEF DESCRIPTION OF THE DRAWINGS

FIG. 1 shows amino acid sequences and genomic construction of Bradeion α and β. (A) Predicted amino acid sequences of human Bradeion α and β (as shown in SEQ ID NOS:2 and 4, respectively). The same amino acids are boxed. The transmembrane region is underlined. ATP/GTP binding site motif A (P-loop; Consensus pattern: (AG)-X(4)-G-K-(ST)) is boxed in yellow color at amino acid numbers 141–166 of Bradeion β. The other GTPase motifs G-2 (DXXG) and G-3 (AKXD) are also boxed in yellow color. (B) Genomics construction of Bradeion α and β. Each exon is shown as a box and $2^{nd}$ and $9^{th}$ exons of Bradeion α are divided and the 3' end and $4^{th}$ exon is deleted in Baredion β.

FIG. 3 shows cancer-specific expression of bradeion genes in colorectal adenocarcinoma cell (T1 to T10); skin cancer cells (T11to T13); and normal cells (N1 to N2). All specimens are from humans. In the figure, "*" refers to the case where both Bradeion α and Bradeion β genes are detected without gene mutation; "ND" refers to the case where detection was impossible due to denaturation of RNA; "Ad (well)" refers to a well differentiated adenocarcinoma; "Ad (mod)" refers to a moderately differentiated adenocarcinoma; "Muc" refers to a mucinouscarcinoma; and "MM" refers to malignant melanoma. Dukes' stage is based on the Dukes' classification. Codon 12 of human K-ras gene (whose wild type sequence is GGT) is indicated if it has been mutated. This mutation is heterozygous.

DETAILED DESCRIPTION OF THE INVENTION

Properties of Bradeion α and β

Figure 2B:
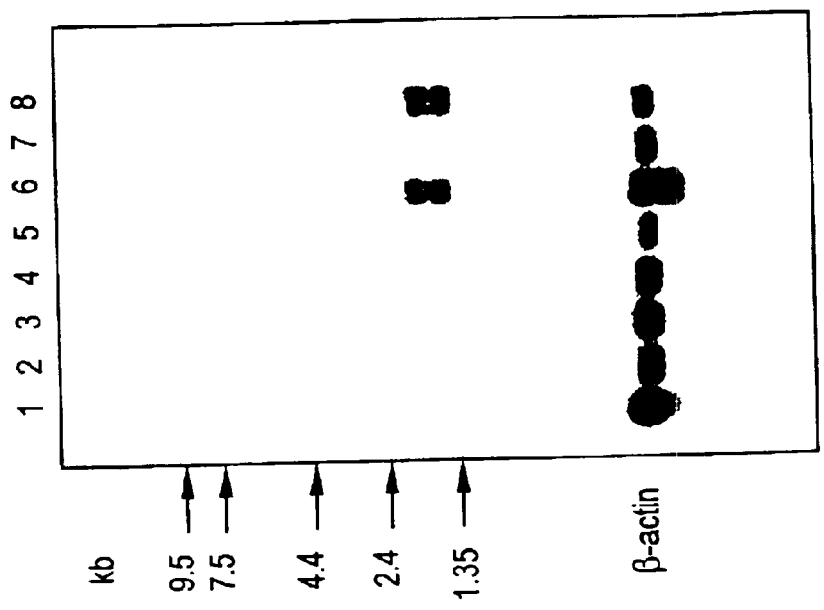
FIG. 2 shows tissue distribution of Bradeion mRNAs. (A) Membranes containing 2 µg/lane of polyadenylated RNA from indicated tissues (MTN™Blots, Clontech, 7760–1 for adult human tissues, 7756-1 for fetal organs) were hybridized with a $^{32}$P-labelde whole region of human Bradeion α cDNA. (B) Northern blots of human cancer cell lines (MTN Blots, Clontech, 7757-1 for human cancer cell line) were hybridized with a $^{32}$P-labeled whole region of human Bradeion α cDNA. Lane 1, Polymyelocytic leukemia, HL-60; Lane 2, HeLa S3; Lane 3, Chronic myologenous leukemia, K-562; Lane 4, Lymphoblastic leukemia, MOLT-4; Lane 5, Burkitt's Lymphoma, Raji; Lane 6, Colorectal adenocarcinoma, SW480; Lane 7, Lung carcinoma, A549; Lane 8, Melanoma, G361. Results of hybridization with β-actin probe are shown below.

Bradeion α and β have the following properties.

(i) it is a transmembranous protein;

(ii) it has a structure characteristic of growth hormone and cytokine receptors (even in a structure of its transmembranous portion) when its structure is determined by a hydrophobicity analysis according to Kyte-Doolittle method;

(iii) it is expressed at a high level in the human adult brain, in less amount in the heart, while it is not expressed in other adult organs or fetus;

(iv) it induces programmed cell death (apoptosis) when over-expressed in cultured human cell lines;

(v) it induces termination of cell division and aging when over-expressed in cultured human normal cells;

(vi) it is located in cytoplasm, and forms an intracellular aggregate when overexpressed; and (vii) besides human adult neurons, it is specifically expressed in a human colorectal cancer cell line or in a skin cancer cell line.

Bradeion α and Bradeion β proteins have the amino acid sequences shown in FIG. 1A (SEQ ID NOS:2 and 4, respectively).

Cloning and Expression of Bradeion α and β cDNAs cDNA coding for bradeion proteins may be obtained as follows.

First, brain tissue is homogenized in a phenol or phenol-chloroform solution containing guanidine isothiocyanate, and subjected to high-speed centrifugation to be separated into an aqueous layer and an organic layer. Total RNA contained in the aqueous layer is precipitated and collected by adding isopropanol, or is collected through sucrose or cesium chloride density-gradient centrifugation. The obtained total RNA is subjected to oligo(dT)-cellulose chromatography to purify mRNA (i.e., poly(A) RNA) therefrom.

Then, cDNA is synthesized from the mRNA in the presence of a reverse transcriptase. The cDNA is provided with suitable restriction sites and inserted into a phage or plasmid vector having the identical restriction sites. The thus-obtained vector is used to transform or transfect E.coli to produce a cDNA library.

Since the cloned cDNA library includes various DNA fragments with information other than that of the DNA of interest, it is necessary to select the DNA of interest. For this purpose, plaque hybridization or colony hybridization may usually be employed. According to such methods, plaques (in the case of a phage vector) or colonies (in the case of a plasmid vector) formed on agar are transferred to a nitrocellulose membrane or a nylon membrane. After being treated with an alkaline solution, they are bound to a radioactive ($^{32}$P) or fluorescence labeling DNA probe that is capable of hybridizing with the DNA of interest, and exposed on an X-ray film, thereby detecting and collecting a plaque or colony containing the DNA of interest. Alternatively, the obtained set of clones may be exposed to an inducer such as isopropyl 1-thio-β-D-galactoside (hereinafter, referred to as "IPTG") to forcibly express proteins. The proteins are then transferred to a nylon membrane or a cellulose membrane, and a specific antibody for the protein of interest is used to immunologically select the corresponding clones.

The cDNA of interest collected from the plaques or colonies that positively reacts with the probe is sequenced by Maxiam-Gilbert method or Sanger-Coulson method.

For cloning and sequencing, for example, methods described in Sambrook et al., Molecular Cloning (1989, Cold Spring Harbor Laboratory Press), Ausubel et al., Current Protocols in Molecular Biology, Green Publishing Company Assoc. and John Wiley Interscience, NY, 1992, etc. may be used.

Specifically, as will be described later in Examples, cDNA library from human adult brain is constructed and thereafter cDNA coding for the bradeion proteins of the invention are collected from the positive clones. As the result of the sequencing analysis, two types of bradeion genes, i.e., Bradeion α and Bradeion β genes, were found which were presumably produced due to alternative splicing. The nucleotide sequences of these genes are included in the sequences shown in SEQ ID NOS: 1 and 3. The Bradeion α and Bradeion β proteins have amino acid sequences shown in FIG. 1A (SEQ ID NOS:2 and 4, respectively), as identified from their nucleotide sequences.

Bradeion α protein was found to have a structure characteristic of an interleukin receptor even in a structure of its transmembranous portion, when subjected to the hydropathy analysis according to Kyte-Doolittle method (J. Mol. Biol., 157 (1): 105–132, 1982). Thus, it has the structure of a transmembrane-type receptor that is presumably involved in the intracellular signaling mechanism. Bradeion α and Bradeion β proteins are also similar to the relationship of the tumor suppression genes p53/p73 in that there are two types of expression modes, i.e., α- and β-types, and in that either of them is prevalent in various organisms. Formation of an intracellular aggregate is very similar to that seen in human nerve retroplasia caused by a triplet repeat gene expressed substance (Igarashi et al., Nature Genetics, 111–117, 1998; Martindale et al., Nature Genetics, 150–154, 1998). Accordingly, it is assumed that the Bradeion α and Bradeion β proteins are greatly associated with specific termination of the division of human nerve cells and/or with maintenance of the function of the nerve cells after development/differentiation in the normal gene expression state.

The human-derived bradeion proteins may be obtained, for example, by using gene recombinant techniques as follows.

Taking account of degeneracy of the genetic codes, a hybridization probe having at least 15, preferably about 20 to about 50 consecutive nucleotides is constructed based on the nucleotide sequence shown in SEQ ID NO:1 or 3 or the amino acid sequence shown in SEQ ID NO:2 or 4. By using this hybridization probe, DNAs coding for the bradeion proteins are screened from a genomic DNA library or cDNA library derived from human brain tissue. The library may be produced by using commercially available vector such as λ ZAPII or pBluescript® cloning vector (Stratagene Cloning Systems). The plaque or colony containing the DNA of interest is selected through plaque hybridization or colony hybridization.

Alternatively, a DNA sequence generally having 15 to 100 consecutive nucleotides complementary to the nucleotides 129–1943 of SEQ ID NO: 1 or the nucleotides 129–1562 of SEQ ID NO:3, is produced as a primer. This primer can be used to conduct polymerase chain reaction (PCR) in the genomic DNA library or cDNA library derived from human brain tissue, thereby specifically amplifying the DNA of interest. PCR can be conducted through at least 20 cycles, preferably at least 30 cycles of: denaturation at 94° C. for 1 min.; annealing at 57° C. for 2 min.; and elongation at 70° C. for 3 min. For the PCR, see the techniques described in Protein Nucleic acid and Enzyme, "Frontier of PCR method—Basic to Applied Techniques" vol. 4(5), April, 1996 Supplement, Kyoritsu Shuppan, Tokyo, Japan.

The cloned or amplified DNA of interest is collected and introduced into an available suitable expression vector. The obtained vector is used to transform a suitable host cell, which is thereafter cultured in a proper medium for expression of the DNA, to isolate and purify the protein of interest.

The following provides preparations of an expression vector containing the above-described DNA, and of a host cell transformed or transfected with the vector.

The vector may be in the form of, for example, plasmid, phage, or virus. Other types of vectors may also be used as long as they are replicable in a host cell. For example, bacterium plasmids (e.g., pBR322, pKC30, pCFM536, etc.), phage DNAs (e.g., λ phage, etc.), yeast plasmids (e.g., pG-1, etc.), or viral DNAs for mammal host cells (e.g., baculovirus, vaccinia virus, adenovirus, SV40 and its derivatives, etc.) may be used.

The vector usually contains a replication origin, a selective marker, a promoter, and, if necessary, may contain an enhancer, a transcription termination sequence (terminator), a ribosome-binding site, a polyadenylation signal, etc.

Where the vector is used for *E.coli*, the replication origin is derived from ColE1, R factor, or F factor. Where the vector is used for yeast, the replication origin is derived from, for example, 2 μm DNA or ARS1. Where the vector is used for a mammalian cell, the replication origin is derived from, for example, SV40, adenovirus, or bovine papilloma virus.

The promoter is a regulator sequence for directing a synthesis of mRNA coding for the DNA of the invention. Representative examples of the promoter include adenovirus or SV40 promoter, *E.coli* lac or trp promoter, phage λ P$_L$ promoter, ADH, PHO5, GPD, PGK or AOX1 promoter (for yeast), and a promoter derived from nuclear polyhedrosis virus (for *Bombyx mori* cell).

The selective marker is a gene for providing a phenotype to the host in order to select transformed host cells. Exemplary selective markers include kanamycin-resistant gene, ampicillin-resistant gene, tetracycline-resistant gene, and the like (when the vector is used for *E.coli*); Leu2, Trp1, Ura3 genes, and the like (when the vector is used for yeasts); and neomycin-resistant gene, thymidine kynase gene, dihydrofolate reductase gene, and the like (when the vector is used for mammalian cells).

Commercially available vectors may be used such as pQE70, pQE60, pQE-9 (Qiagen), pBluescript II KS, ptrc99a, pKK223-3, pDR540, pRIT2T (Pharmacia), and pET-11 a (Novagen) as bacterium vectors; and pXT1, pSG5 (Stratagene), pSVK3, pBPV, pMSG and pSVL SV40 (Pharmacia) as eukaryote vectors.

The bradeion DNA may be introduced into the vector by any means. The vector preferably contains a polylinker with various restriction sites, or a unique restriction site. The DNA is inserted into a particular restriction site(s) of the vector where it has been cleaved with a particular restriction endonuclease(s).

The expression vector containing the bradeion DNA with a regulatory sequence can be used to transform or transfect a suitable host cell, thereby expressing and producing the human bradeion protein in the host cell.

The host cell is, for example, a bacterial cell (e.g., *E.coli, streptomyces*, or *Bacillus subtilis*), an eukaryotic cell (e.g., *Aspergillus* strain), an yeast cell (e.g., *Saccharomyces cerevisiae*, or methanol-assimilating yeast), an insect cell (e.g., *Drosophila* S2 or *Spodoptera* Sf9), and a mammalian cell including cultured human cell (e.g., CHO, COS, BHK, 3T3, or C127).

Transformation or tranfection may be conducted by a known method such as calcium chloride/rubidium chloride method, calcium phosphate method, DEAE-dextran-mediated transfection, or electroporation.

The human-derived bradeion protein can be obtained by culturing the host cells which have been transformed or transfected as described above under the control of the promoter, and by collecting the produced protein of interest. The host cell is amplified or grown to a proper cell density. Then, the promoter is induced by shifting the temperature or by chemical induction (with IPTG, etc.). The cell is further cultured for a predetermined period. Where the protein of interest is secreted extracellularly, it can directly be obtained from the medium. Where the protein of interest is present intracellularly, the cell can be disrupted by physical means (e.g., sonication or mechanical disruption) or by chemical means (e.g., lyzozyme or cytolytic agent). Then the protein of interest is purified. The protein may partially or completely be purified from the culture medium containing the recombinant cells or an extracted solution thereof, by using routine techniques such as ammonium sulfate or ethanol precipitation,; acid extraction, anion or cation exchange chromatography, hydrophobic interaction chromatography, affinity chromatography, gel filtration chromatography, HPLC, electrophoresis, and chromatofocusing, alone or in combination.

Bradeion α and β Ribozymes and Its Use for Treatment of Cancers

The ribozymes of the invention can be synthesized by methods as disclosed by T. Kuwabara et al. (Proc. Natl. Acad. Sci. USA 95:1886–1891, 1999). Their sequences has the same structure as the Brad-α1 (hammerhead ribozyme) or the heterodimeric ribozyme composed of Brad-β3L and Brad-β3R shown in FIG. 1A, except that the substrate binding site alters depending on a sequence of a substrate. The substrate binding site has a sequence complementary to a substrate sequence, for example, RNA sequence corresponding to nucleotide numbers 569–583, 588–602, 595–609 or 699–713 of SEQ ID NO:1, or nucleotide numbers 108–122, 157–171, 304–318 and 378–392 of SEQ ID NO:3.

The ribozymes of the invention is preferably a hammerhead ribozyme. This enzyme is one of the smallest catalytic RNAs (Symons, R. H. *Ann. Rev. Biochem.*, 61: 641–671 (1992)), and has been tested as potential therapeutic agents and their mechanisms of action have been studied (Symons, R. H. *Ann. Rev. Biochem.*, 61: 641–671 (1992); Zhou, D.-M. & Taira, K. *Chem. Rev.* 98: 991–1026 (1998); Eckstein F. & Lilley D. M. J. (eds.) Catalytic RNA, Nucleic Acids and Molecular Biology, vol. 10 (Springer-Verlag, Berlin, 1996)). The hammerhead ribozyme can cleave oligoribonucleotides at specific sites (namely, after the sequence NUX, where N and X can be A, G, C or U and A, C or U, respectively, with the most efficient cleavage occurring after a GUC or GUA triplet) (Shimayama, T., Nishikawa, S. & Taira, K. *Biochemistry* 34: 3649–3654 (1995)). To date, numerous studies directed towards the application of ribozymes in vivo have been performed and many successful experiments, aimed at the exploitation of ribozymes for the suppression of gene expression in different organisms, have been reported (Sullenger, B. A. & Cech, T. R. *Science* 262: 1566–1569 (1993); Yu, M., et al. *Proc. Natl. Acad Sci. USA* 92: 699–703 (1995); Bertrand, E. et al. *RNA* 3: 75–88 (1997); Kawasaki, H., et al. *Nature* 393: 284–289 (1998); Kuwabara, T., et al. *Nature Biotechnol.* 16: 961–965 (1998); Kuwabara, T., et al. *Mol. Cell* 2: 617–627 (1998); Plehn-Dujowich, D. & Altman, S. *Proc. Natl. Sci. Acad. USA* 95: 7327–7332 (1998); Koseki, S., et al. *J. Virol.* 73: 1868–1877 (1999); Tanabe, T. et al. *Nature* 406: 473–474 (2000)). These literature are incorporated herein by reference in their entirety.

The ribozymes of the invention can be synthesized by usual nucleic acid synthesis methods, preferably be chemically synthesized by a DNA/RNA synthesizer.

Expression Vector Comprising DNA Encoding Ribozyme

This invention also provides an expression vector comprising DNA encoding the ribozyme. Examples of the vector constructing an expression system include plasmid vectors such as pUC19 (Takara Shuzo, Kyoto), pGREEN LANTERN (Life Tech Oriental, Tokyo) and pHaMDR (HUMAN GENE THERAPY 6:905–915 (July 1995)), and vectors for gene therapy such as adenovirus vector and retrovirus vector.

The above vector may comprise a promoter sequence upstream of the ribozyme sequence. The promoter sequence is an element to control the expression of the ribozyme. Examples of the promoter include virus promoter (e.g. SV40 promoter), phage promoter (e.g. λ PL promoter), pol III promoter (e.g. human tRNA promoter such as tRNA$^{val}$ promoter, adenovirus val promoter) etc. In this invention, pol III promoter, particularly tRNA promoter is preferably used. The sequence of tRNA$^{val}$ promoter is for example:

accguugguu uccguagugu agugguuauc acguucgccu aacacgc-gaa agguccccgg uucgaaaccg ggcggaaaca aagacagucg cuuuu (SEQ ID NO:15); or accgttggtt tccgtagtgt agtggttatc acgttcgcct aacacgcgaa aggtc-cccgg ttcgaaaccg ggcactacaa aaaccaactt t (SEQ ID NO: 16).

In addition, the vector of this invention may comprise a terminator sequence downstream of the chimeric molecule. Any terminator sequence is used, provided that the sequence is one that terminates transcription. For example, UUUUU can be used as a terminator sequence. The vector may optionally comprise a selectable marker gene or reporter gene such as an antibiotic resistant gene (e.g., Armp.$^r$, Neo$^r$) or an auxotrophy. complementing gene.

Pharmaceutical Composition and Treatment of Cancers

Furthermore, this invention provides a pharmaceutical composition comprising a set of an expression vector comprising Bradeion α ribozyme and an expression vector comprising Bradeion β ribozyme, as an active ingredient. The pharmaceutical composition may include a pharmaceutically acceptable carrier, e.g. dilutent such as physiological saline or buffer. The pharmaceutical composition of the invention can be employed for treatment of a cancer including colorectal cancer and malignant melanoma. This is based on the finding that the expression of bradeion is specific for colorectal cancer and malignant melanoma (skin cancer).

The method of introducing the vector containing DNA encoding the ribozyme into cell includes calcium phosphate method, electroporation, lipofection, microinjection, particle gun, the use of liposome (e.g. Mamoru Nakanishi et al., *Proteins, Nucleic Acids & Enzymes*, Vol. 44, No. 11, 1590–1596 (1999)), and the like. For example, part of cells may be removed from a diseased site to be subjected to in vitro gene transfer and subsequently transplant back into tissue, or a vector may be directly introduced into the tissue of the diseased site. When a virus vector is used, the virus titer is usually more than approx. $10^7$ pfu/ml.

The bradeion α and β seem to allow survival of cranial nerve cells of the central nervous system in non-dividing state via neuro-stimulating transmission. It seems to be important that over-expression of the bradeion genes controls cell fate: apoptosis or carcinogenesis, and that normally the expression ratio of the α-type to the β-type is maintained (at a ratio of 10:1 in a normal cranial nerve cell). It was also suggested that depending on changes in the expression ratio (e.g., 1:1), it may induce development of cancer. Accordingly, the bradeion proteins are presumed to play an important role in controlling cell fate (termination, apoptosis, and/or carcinogenesis), and also to determine long-term survival of cranial nerve cells in non-dividing state in human adult central nervous system.

This invention is based on the finding that when the bradeion transcripts (mRNAs) are cleaved with a set of bradeion α and β ribozymes then proliferation of a cancer is almost completely inhibited or suppressed. Thus, the antisense-ribozymes of this invention may be used for treating a subject with a cancer associated with the bradeions (e.g., human colorectal carcinoma, or human skin cancer such as malignant melanoma).

EXAMPLES

Hereinafter, the present invention will be illustrated by the following examples. The present invention, however, is not intended to be limited to these examples.

Example 1

Cloning and Sequencing of cDNA Coding for Human Bradeion

First, a cDNA library from a human adult brain was constructed using the plasmid vector pCMV SPORT1 (Life. Technologies, Inc., USA) which is capable of linking with a CMV promoter for expressing in an eukaryotic cell. The adult brain was obtained from a 36-year-old white Caucasian American female, and mRNA (poly(A) RNA) was extracted therefrom with TRIzol® reagent (Life Technologies, Inc.) and purified with MESSAGEMAKER® reagent (Life Technologies, Inc.). Then double stranded cDNA synthesis and library construction were initiated by SuperScript plasmid system.

The prepared mRNA (poly(A) RNA) was linked with NotI primer adapter at its 3'-terminus. Then, a double stranded cDNA was synthesized according to a standard method using SuperScript II reverse transcriptase and T4 DNA polymerase. The 5'-terminus of the cDNA was linked with SalI adapter and 3'-terminus was treated with NotI restriction enzyme so that the cDNA fragment had restriction sites SalI and NotI at each end. The cDNA was separated in sizes by gel filtration chromatography to select and fractionate cDNA having a size of 1 kb or more. The obtained set of cDNA fragments was inserted, by a standard method, into the plasmid vector pCMV SPORT1 that also had been cleaved with SalI and NotI; thereby producing circular plasmids. These plasmids were introduced into *E.coli* DH12S cells (Life Technologies, Inc.) by an electroporation method and amplified to construct a library.

The resulting *E.coli* strains were grown on ampicillin-containing LB agar medium to form colonies. Biodyne A nylon membrane (Pall Corp., US) treated with 10 mM IPTG was placed in close contact with the colonies and left at 37° C. for 2 hours. The nylon membrane was reacted with the antibody CE5 that specifically recognizes cranial nerve cells. Positive clones were selected using picoBlue® Immunoscreening Kit (Stratagene, US).

Plasmid DNA was collected from the obtained positive clones to be used as a $^{32}$P-labeled probe, which was hybridized with nylon membranes with mRNAs specific for different human organs (MTN blot, CLONTECH Lab., Inc.) to test whether the probe was specific for the brain. The nucleotide sequences of the cDNAs were determined by sequencing analysis and compared with homologous sequences deposited with the GenBank. Only the one that was completely novel was deposited with the GenBank as a sequence of interest. The determined nucleotide sequence of the Bradeion α cDNA is included in the sequence shown in SEQ ID NO:1 (GenBank Accession No. AB002110). The amino acid sequence of the Bradeion α determined based on this nuclebtide sequence is shown in SEQ ID NO:2 (FIG. 1A). The coding region was at the positions 97–720 in the nucleotide sequence of SEQ ID NO:1. DNA containing Bradeion α cDNA was deposited under the terms of Budapest Treaty with the National Institute of Bioscience and Human-Technology, Agency of Industrial Science and Technology (Higashi 1-1-3, Tsukuba-shi, Ibaraki-ken 305–8566, Japan) on Oct. 19, 1999 as FERM BP-6922.

Based on the above-described sequence of Bradeion α cDNA, 5'-terminal primers (described below) were synthesized to systematically screen relevant genes. For this purpose, Gene Trapper Positive Selection system (Life Technologies, Inc.) was used to screen the above-described gene library with the synthesized oligonucleotides and magnet beads. The sequences of the oligonucleotides used were:

5'-ctgagcaagttcgtgaaggatttc-3' (SEQ ID NO:17) and

5'-cagtcctctgacaaccagcagta-3' (SEQ ID NO:18).

As a result, a gene was detected which was named Bradeion β and whose nucleotide sequence is included in the sequence shown in SEQ ID NO:3 (GenBank Accession No. AB008753). The coding region was at the positions 128–1562. The amino acid sequence of Bradeion β determined based on this nucleotide sequence is shown in SEQ ID NO:4 (FIG. 1A).

Example 2

Characterization of Bradeion α and Bradeion β Proteins (1) Localization of Bradeion Proteins Hybridization with the nylon membranes with mRNAs specific for different human organs (MTN blot, CLONTECH Lab., Inc.) indicated a high level expression only in the human adult brain, and a low level of expression in the heart ($\leq$10% of the expression level in the brain). No expression was seen in other organs (spleen, lung, liver, skeletal muscle, kidney and pancreas) or in human fetal brain, lung, heart and kidney. Both of the α- and β-types were expressed in the adult brain. See FIG. 2A and B. The difference in types was due to the gene duplication in the adjacent area (17q23) of human chromosome.

(2) Correlation of Bradeion α and Bradeion β Genes to Cancers

Figure 2A:
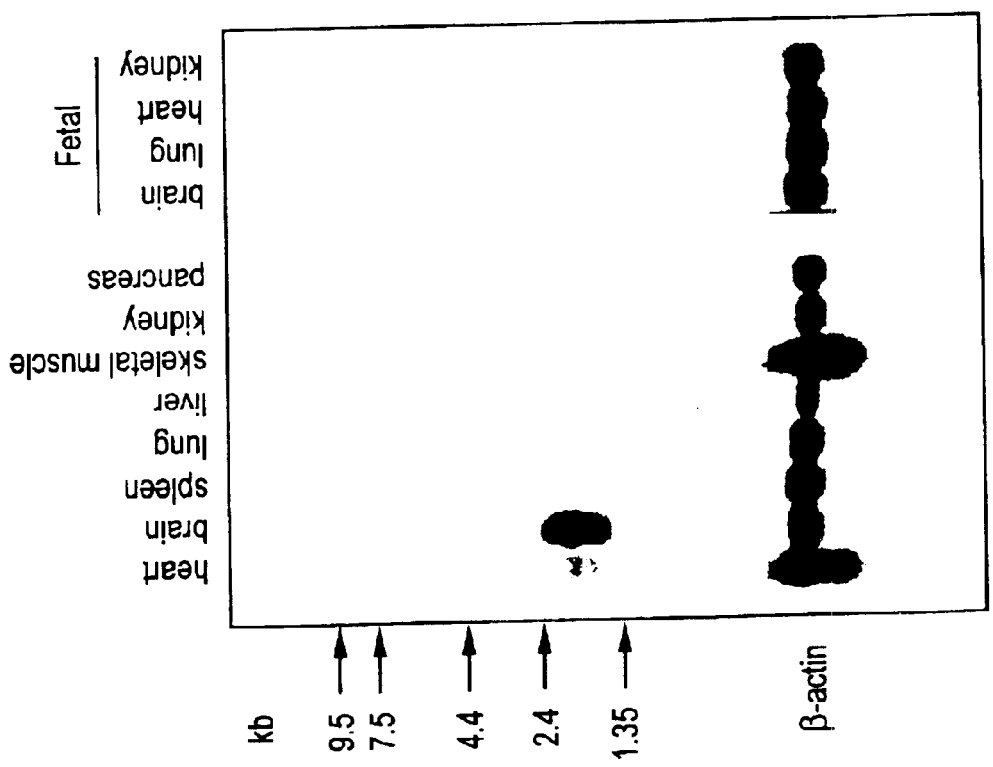

FIG. 2B shows the results of Northern blot regarding expression of Bradeion α and Bradeion β genes in different cultured human cancer cells. Specific expressions (signals) were found only in Lane 8 (melanoma cell line G361) and Lane 6 (colorectal adenocarcinoma SW480).

Specimens from human patients (i.e., specimens from pathologic tissues) were used for detection of the cancer-specific expression. As shown in FIG. 3, the specific expression. was observed in 10 specimens having colorectal adenocarcinoma (T1 to T10; indicated as Ad), and in 3 specimens having skin cancer (T11 to T13; indicated as Muc and MM).

Example 3

Ribozyme-mediated supresion of Bradeion α and β

(1) Design of tRNA$^{val}$-embedded Ribozymes

Figure 4A:
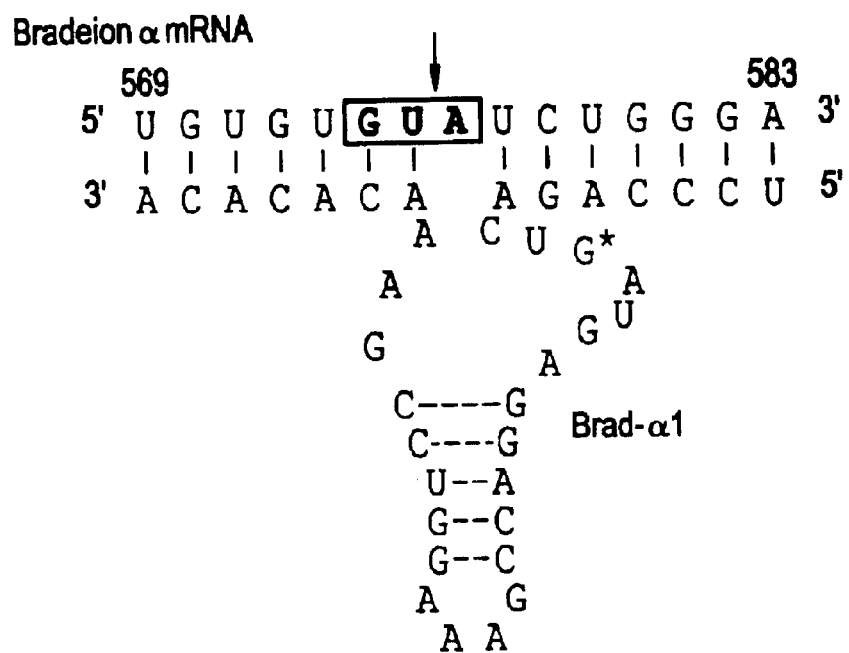
FIG. 4 shows hammerhead ribozymes specific for Bradeion α and β. (A) Secondary structure of the hammerhead ribozyme specific for Bradeion α and β mRNA (SEQ ID NOS 19–23, respectively). Ribozyme-mediated cleavage site is shown in black box. The inactive differed from the active ribozymes by a single G* to A mutation in the catalytic core. The formation of active forms is favored because perfect base paring occurs only in the case of active complexes. (B) G2 growth arrest in colorectal carcinoma cells (SW480) transfected by Bradeion-specific ribozymes and its derivatives shown by flow cytometric cell-cycle analysis. Cells were stained with propidium iodide to show cell-cycle distribution by DNA content. Ten thousand cells were tested in this analysis. G0/G1, S, and G2/M phases of the cell cycle are indicated as 2n and 4n. 1; control SW480, 2; SW480 cells transfected with an inactive ribozyme, 3; SW480 cells transfected only with Bradeion β-specific ribozyme (Brad-α3), 4; SW480 cells transfected only with Bradeion β-specific ribozyme (Brad-β3), 5–9; SW480 cells transfected with Brad-α and Brad-β ribozymes (5, Brad- α3 +Brad-β1; 6, Brad-α3+Brad-β2; 7, Brad-α3 +Brad-β3; 8, Brad-α4 +Brad-β2; 9, Brad-α4+, Brad-β3). (C) RT-PCR analysis of Bradeion mRNAs of each cell line described above. PCR products were subjected to electrophoresis on 2% agarose gel. (D) Growth suppression of colorectal carcinoma cells (SW480) transplanted in nude mice by Bradeion-specific ribozymes.

Ribozymes used in this study were constructed according to the methods as described by T. Kuwabara et al. ("tRNA Val-heterodimeric maxizymes with high potential as gene inactivating agents: simultaneous cleavage at two sites in HIV-1 Tat mRNA in cultured cells," Proc. Natl. Acad. Sci. USA, 95:1886–1891, 1999) and had a tRNA$^{val}$ promoter sequence at the 5' end of the ribozyme. The target sequences of these ribozymes specific for Bradeion α mRNA are the followings: Brad-α1: nucleotide 569–583 of Bradeion α clone; : Brad-α2: nucleotide 588–602; Brad-α3: nucleotide 595–609; Brad-α4: nucleotide 699–713. These ribozymes are represented by SEQ ID NOS:5, 6, 7 and 8, respectively. The target sequences of these ribozymes specific for Bradeion β mRNA are as follows: Brad-β1: nucleotide 108–122 of Bradeion β clone;: Brad-β2: nucleotide 157–171; Brad-β3: nucleotide 304–318; Brad-β4: nucleotide 378–392. These ribozymes are represented by SEQ ID NOS:9, 10, 11 and 12, respectively. Furthermore, a heterodimeric ribozyme which was composed of Brad-β3L and Brad-β3R was constructed by the methods of T. Kuwabara et al. (supra). The sequences of these ribozymes are shown in FIG. 4A (SEQ ID NOS:13 and 14, respectively).

(2) Cells, Transfection and Cell-cycle Analysis

Human colorectal adenocarcinoma cell line (SW480) was obtained from ATCC 10801 University Blvd. Manassas, Va. 20110–2209 USA and cultured in Leibovitz's L-15 medium supplemented with 10% fetal bovine serum. As negative controls, the other cell lines were used such as COS cells and HeLa cells, in which Bradeion genes are not expressed.

Transfections were carried out with the SupperFect Transfection Reagent (Qiagen, Valencia, Calif.), as recommended by the manufacturer. Ribozyme-transfected SW480 cells were selected by incubation with G418, and ribozyme derivatives-transfected cells were selected with G418 (500 μg/ml media) and hygromycin B (250 μg/ml media) (Life Technologies, Rockville, Md.), for more than 4 weeks. As controls, inactive ribozymes and derivatives were transfected and selected as describes above. For flow cytometry analysis, cells were pelleted and resuspended in 1 ml of PBS containing 2 μg/ml RNase and 50 mg/ml propidium iodide, and incubated for more than 30 min at 37° C. The profile of cells in the G0/G1, S and G2/M phases of the cell cycle were analysed by using EPICS ELIFE ESP (Beckman Coulter, Co. Ltd.) accoding to the instructions by manufacturers.

(3) Growth of Colon Cancer xenografs in athymic Mice

The stable transformants and parental cell lines (SW480; $5\times10^5$ cells) were subcutaneously inoculated into nude mice (n=10 for each transformants and the parental cell line; female, 8 weeks, BALB/cA-nu, Clea Japan Inc. Tokyo). The growth rates of the cells were estimated by measuring the size of tumor lesions after inoculation. The size was calculated by equation, $V=\frac{1}{2}\times A\times B^2$, in which A and B are the experimental measurements in mm of length and width, respectively. All experiments on laboratory animals were performed in accordance with the care and use guidelines of the Central Institute for Experimental Animals, Kawasaki, Japan.

(4) Results

Bradeion-alpha and beta specific ribozymes were transfected into SW480 cells (FIG. 4). The doubling time of each cell line was; 20–24 hours for origina SW480 (control), 26 hours for the cells transfected with the inactive ribozyme, average 38 hours for the cells with Brad-α ribozymes, average 48 hours in the cells with Brad-α ribozymes, 373 or more in the cells with Brad-α and Brad-β ribozymes. FIG. 4B demonstrates flow cytometry analysis of selected cell lines. The control cells (lane 1) and the cells transfected with inactive ribozyme (lane 2) showed the wild-type phenotype of cell population in each phase (G0/G1, S and G2/M), with up to 70% cell population at G0/G1 phase (2n) and 15% at G2/M phase (4n).

Figure 4B:
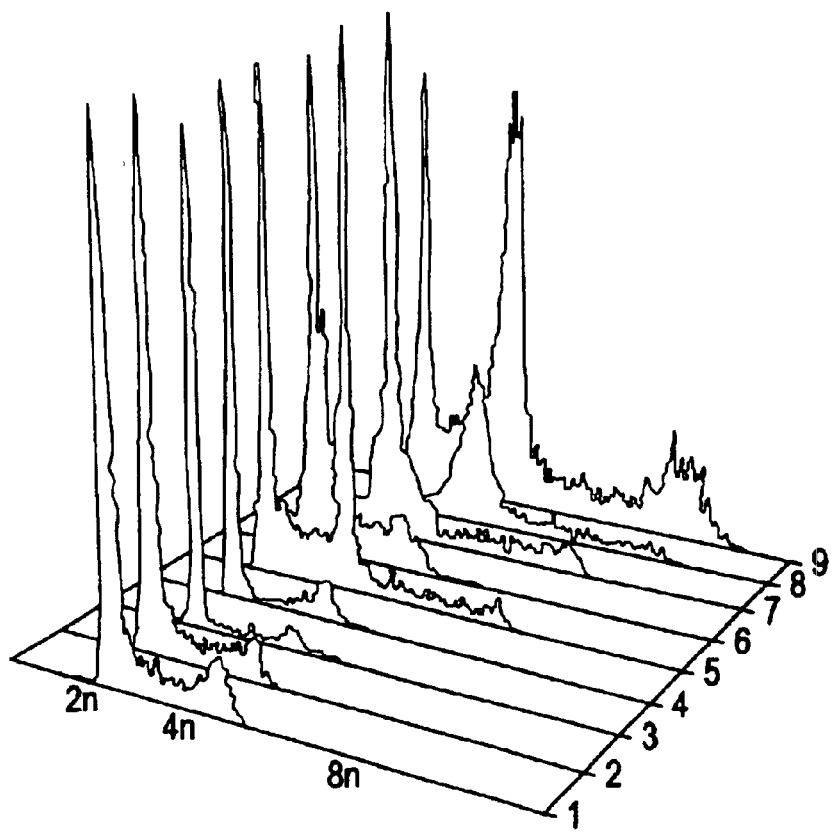

In contrast the cells with Brad-α or Brad-β ribozymes showed irreverent late S clusters in cell cycle (FIG. 4B, Lanes 3 and 4). The transformants with Brad-α and Brad-β ribozymes showed significantly different phenotype, with slower cell growth (over 300 hours doubling time compared to 20–24 hours doubling time of control SW480 cells and the cell transfected with inactive ribozyme. Flow cytometry analysis demonstrated 8n peak (8–12% population) with increased cell population of G2/M phase (lanes 5–9, maximum 68% in lane 9).

Figure 4C:
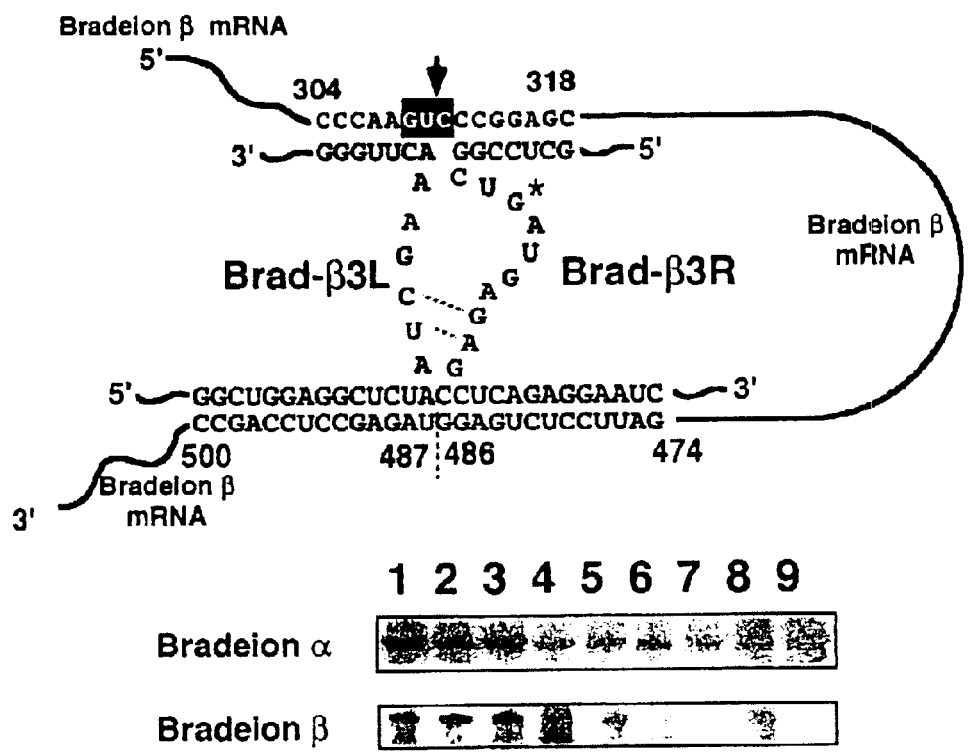

To examine levels of both of Bradeion α and B mRNAs, the present inventor performed RT-PCR analysis. As shown in FIG. 4C, the level of Bradeion in SW480 cells transfected with ribozymes was drastically lower than in control SW480 cells and/or SW480 cells transfected with inactive ribozyme (lanes 1 and 2). The level of Bradeion β mRNA did not alter in the Brad-α ribozyme expressing SW480 cells (lane 2). These results indicate that this hammerhead ribozyme cleaved only Bradeion α specifically. In contrast, in the SW480 cells with Brad-β ribozyme, the level of Bradeion β mRNA was decreased compared with the control cells (lane 1), the cells with inactive ribozyme (lane 2), and the cells with Brad-α ribozyme (lane 3). The level of Bradeion α mRNA did not alter in the cells with Brad-β ribozyme. Both levels of Bradeion α and β mRNAs in the cells with both Brad-α and Brad-β ribozymes were decrease compared with control and inactive ribozyme expressing SW480 cells (lanes 5–9). Bradeion α and β play critical roles in promotion of transition from G2 phase to M phase.

Figure 4D:
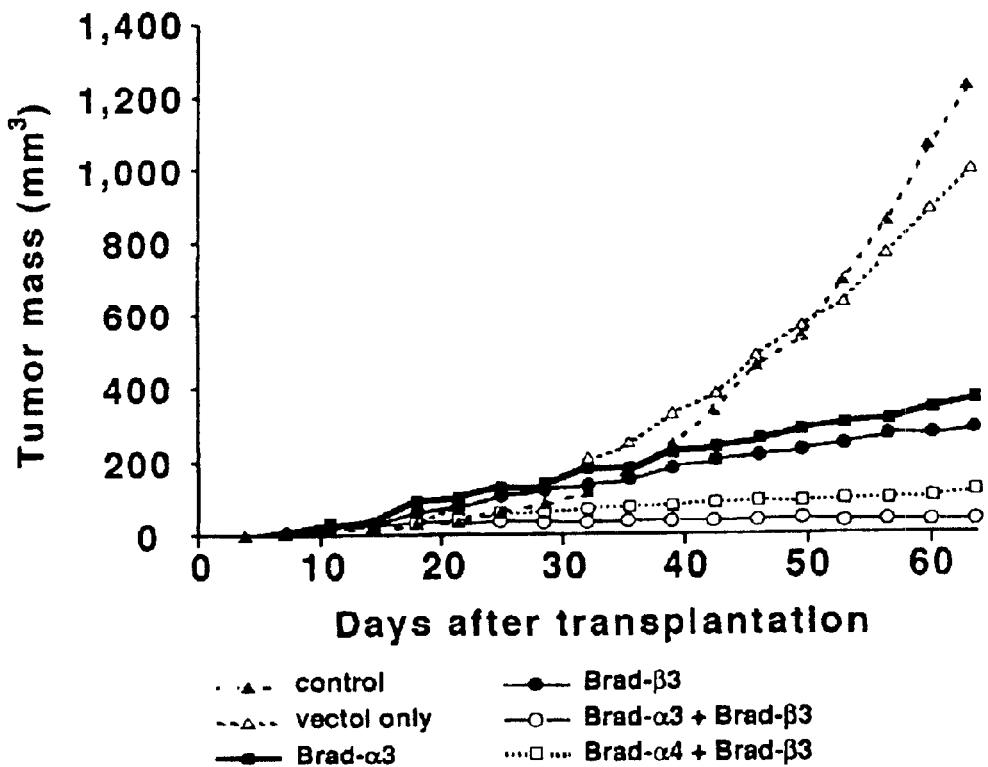

Heterotopic transplantation of the SW480 cells as xenografts in athymic nude mice resulted in the rapid development of progressive tumor nodules (FIG. 4D). Bradeion-specific ribozymes (Brad-α3, Brad-α4, Brad-α3) significantly suppressed tumor growth of SW480 cells in mice. The results were compatible with those of flow cytometirc and RT-PCR analyses (FIGS. 4B and 4C). These results were not observed when the other cell lines were used.

The bradeion α and β ribozymes can be employed for gene therapy of cancers including human colorectal cancer and malignant melanoma.

All publications (including patent applications) cited herein are incorporated herein by reference in their entirety.

The following are information on SEQ ID NOS:1, 3, 5 to 14 described herein:

```
SEQ ID NO:1:
agcatcaaaa caaggctgtt tctgtgtgtg aggaactttg cctgggagat aaaattagac      60
ctagagcttt ctgacaggga gtctgaagcg tgggacatgg accgttcact gggatggcaa     120
gggaattctg tccctgagga caggactgaa gctgggatca agcgtttcct ggaggacacc     180
acggatgatg agaactgag caagttcgtg aaggatttct caggaaatgc gagctgccac      240
ccaccagagg ctaagacctg gcatccagg ccccaagtcc cggagccaag gccccaggcc      300
ccggacctct atgatgatga cctggagttc agaccccct cgcggcccca gtcctctgac      360
aaccagcagt acttctgtgc cccagcccct ctcagcccat ctgccaggcc ccgcagccca     420
tggggcaagc ttgatcccta tgattcctct gaggtagagc ctccagccct gcctttgcct     480
ttcagtgggc tgctgcagga agaccgggg cagggagcag agtgtgtgtg tgtgtgtgtg      540
tgtgtgtgtg tgtgtgtgtg tttgtgtgtg tgtgtatctg ggacctattt cagtcctgtg     600
tcagccctag ctccaagata tctgcccca agggcactga aaatttgcag tttcagcaag      660
ggcaggaggc ccagctggtg gcctcagatg ggaactcaca gaagtctggc actgctttt      720
taaggctggg gcaaaggcct gaaagggaga gaagattggc gctgggtgcc ggggcccctt     780
tggctcctca ccgtgatgca ttctgccttc ctgtctacta ggatgacaag gagtatgtgg     840
gctttgcaac cctccccaac caagtccacc gaaagtccgt gaagaaaggc tttgacttta     900
ccctcatggt ggcaggagag tctggcctgg gcaaatccac acttgtcaat agcctcttcc     960
tcactgatct gtaccgggac cggaaacttc ttggtgctga agagaggatc atgcaaactg    1020
tggagatcac taagcatgca gtggacatag aagagaaggg tgtgaggctg cggctcacca    1080
ttgtggacac accaggtttt ggggatgcag tcaacaacac agagtgctgg aagcctgtgg    1140
cagaatacat tgatcagcag tttgagcagt atttccgaga cgagagtggc ctgaaccgaa    1200
agaacatcca agacaacagg gtgcactgct gcctgtactt catctcaccc ttcggccatg    1260
ggctccggcc attggatgtt gaattcatga aggccctgca tcagcgggtc aacatcgtgc    1320
ctatcctggc taaggcagac acactgacac ctccgaagt ggaccacaag aaacgcaaaa     1380
tccgggagga gattgagcat tttggaatca agatctatca attcccagac tgtgactctg    1440
atgaggatga ggacttcaaa ttgcaggacc aagccctaaa ggaaagcatc ccatttgcag    1500
taattggcag caacactgta gtagaggcca gagggcggcg agttcggggt cgactctacc    1560
cctgggcat cgtggaagtg gaaaacccag ggcactgcga ctttgtgaag ctgaggacaa     1620
tgctggtacg tacccacatg caggacctga aggatgtgac acgggagaca cattatgaga    1680
actaccgggc acagtgcatc cagagcatga cccgcctggt ggtgaaggaa cggaatcgca    1740
agtatgacca gaagcagga caaagctggc aggggagat cccaagccta gccttgggtg     1800
agaccaagcc ctactttgt tcttctatag gccctgggct caatctaagc gggtgctggg     1860
gtcctcctcg ccttatcaac ccttttctcc ctttagcaaa ctgactcggg aaagtggtac    1920
cgacttcccc atccctgctg tcccaccagg gacagatcca gaaactgaga agcttatccg    1980
agagaaagat gaggagctgc ggcggatgca ggagatgcta cacaaaatac aaaaacagat    2040
gaaggagaac tattaactgg cttttcagccc tggatattta aatctcctcc tcttcttcct    2100
gtccatgccg gccctcca gcaccagctc tgctcaggcc ccttcagcta ctgccacttc     2160
gccttacatc cctgctgact gcccagagac tcagaggaaa taaagtttaa taatctgta    2220
```

-continued

SEQ ID NO:3:
```
gaaaggagca agccaggaag ccagacaaca acagcatcaa acaaggctg tttctgtgtg      60
tgaggaactt tgcctgggag ataaaattag acctagagct ttctgacagg gagtctgaag    120
cgtgggacat ggaccgttca ctgggatggc aagggaattc tgtccctgag acaggactg     180
aagctgggat caagcgtttc ctggaggaca ccacggatga tggagaactg agcaagttcg    240
tgaaggattt ctcaggaaat gcgagctgcc acccaccaga ggctaagacc tgggcatcca    300
ggccccaagt cccggagcca aggccccagg ccccggacct ctatgatgat gacctggagt    360
tcagaccccc ctcgcggccc cagtcctctg acaaccagca gtacttctgt gccccagccc    420
ctctcagccc atctgccagg ccccgcagcc catggggcaa gcttgatccc tatgattcct    480
ctgaggatga caaggagtat gtgggctttg caaccctccc caaccaagtc caccgaaagt    540
ccgtgaagaa aggctttgac tttacccctca tggtggcagg agagtctggc ctgggcaaat    600
ccacacttgt caatagcctc ttcctcactg atctgtaccg ggaccggaaa cttcttggtg    660
ctgaagagag gatcatgcaa actgtggaga tcactaagca tgcagtggac atagaagaga    720
agggtgtgag gctgcggctc accattgtgg acacaccagg ttttgggat gcagtcaaca    780
acacagagtg ctggaagcct gtggcagaat acattgatca gcagtttgag cagtatttcc    840
gagacgagag tggcctgaac cgaaagaaca tccaagacaa caggggtgcac tgctgcctgt    900
acttcatctc acccttcggc catgggctcc ggccattgga tgttgaattc atgaaggccc    960
tgcatcagcg ggtcaacatc gtgcctatcc tggctaaggc agacacactg acacctcccg   1020
aagtggacca caagaaacgc aaaatccggg aggagattga gcattttgga atcaagatct   1080
atcaattccc agactgtgac tctgatgagg atgaggactt caaattgcag gaccaagccc   1140
taaaggaaag catcccattt gcagtaattg cagcaacac tgtagtagag gccagagggc   1200
ggcgagttcg gggtcgactc taccctggg gcatcgtgga agtggaaaac ccagggcact   1260
gcgactttgt gaagctgagg acaatgctgg tacgtaccca catgcaggac ctgaaggatg   1320
tgacacggga gacacattat gagaactacc gggcacagtg catccagagc atgacccgcc   1380
tggtggtgaa ggaacggaat cgcaacaaac tgactcggga aagtggtacc gacttcccca   1440
tccctgctgt cccaccaggg acagatccag aaactgagaa gcttatccga gagaaagatg   1500
aggagctgcg gcggatgcag gagatgctac acaaaataca aaaacagatg aaggagaact   1560
attaactggc tttcagccct ggatatttaa atctcctcct cttcttcctg tccatgccgg   1620
cccctcccag caccagctct gctcaggccc cttcagctac tgccacttcg cctaacatcc   1680
ctgctgactg cccagagact cagaggaaat aaagtttaat aaatctgtag gtggc         1735
```

SEQ ID NO:5 (Brad-α 1):
UCCCAGACUG AGGACCGAAA GGUCCGAAAC ACACA                                 35

SEQ ID NO:6 (Brad-α 2):
GACACAGCUG AUGAGGACCG AAAGGUCCGA AACUGAAA                              38

SEQ ID NO:7 (Brad-α 3):
UAGGGCUCUG AUGAGGACCG AAAGGUCCGA AACACAGG                              38

SEQ ID NO:8 (Brad-α 4):
AGUGCCACUG AUGAGGACCG AAAGGUCCGA AACUUCUG                              38

SEQ ID NO:9 (Brad-β 1):
CGCUUCACUG AUGAGGACCG AAAGGUCCGA AACUCCCU                              38

SEQ ID NO:10 (Brad-β 2):
CCUCAGGCUG AUGAGGACCG AAAGGUCCGA AACAGAAU                              38

SEQ ID NO:11 (Brad-β 3):
GCUCCGGCUG AUGAGGACCG AAAGGUCCGA AACUUGGG                              38

-continued

SEQ ID NO:12 (Brad-β 4):
GUCAGAGCUG AUGAGGACCG AAAGGUCCGA AACUGGGG        38

SEQ ID NO:13 (Brad-β 3L):
GGCUGGAGGC UCUAAUCGAA ACUUGGG        27

SEQ ID NO:14 (Brad-β 3R):
GCUCCGGCUG AUGAGAGCCU CAGAGGAAUC        30

What is claimed is:

1. A set of ribozymes which comprises at least one ribozyme capable of binding and cleaving Bradeion α mRNA which corresponds to DNA comprising a nucleotide sequence shown in SEQ ID NO:1, and at least one ribozyme capable of binding to and cleaving Bradeion β mRNA which corresponds to DNA comprising a nucleotide sequence shown in SEQ ID NO:3, wherein said ribozyme capable of binding to and cleaving Bradeion α mRNA targets a sequence selected from the group consisting of RNA sequences corresponding to nucleotide numbers 569–583, 588–602, 595609 and 699–713 of SEQ ID NO:1, and said ribozyme capable of binding and cleaving Bradeion β mRNA targets a sequence selected from the group consisting of RNA sequences corresponding to nucleotide numbers 108–122, 157–171, 304–318 and 378–392 of SEQ ID NO:3.

2. A set of ribozymes of claim 1 wherein each of said ribozymes is a hammerhead ribozyme.

3. A set of ribozymes of claim 1 wherein each of said ribozymes is a monomeric or heterodimeric ribozyme.

4. A set of ribozymes which comprises at least one ribozyme capable of binding and cleaving Bradeion α mRNA which corresponds to DNA comprising a nucleotide sequence shown in SEQ ID NO:1, and at least one ribozyme capable of binding to and cleaving Bradeion β mRNA which corresponds to DNA comprising a nucleotide sequence shown in SEQ ID NO:3, wherein said ribozymes are a combination of at least one ribozyme selected from the group consisting of ribozymes of SEQ ID NO:5, SEQ ID NO:6, SEQ ID NO:7 and SEQ ID NO:8, and at least one ribozyme selected from the group consisting of ribozymes of SEQ ID NO:9, SEQ ID NO:10, SEQ ID NO:11 and SEQ ID NO:12 and a heterodimeric ribozyme that is composed of an RNA sequence of SEQ ID NO:13 and an RNA sequence of SEQ ID NO:14.

5. A set of ribozymes of claim 4 wherein said ribozymes are a combination of a ribozyme of SEQ ID NO:7 and a ribozyme of SEQ ID NO:9, 10 or 11.

6. A set of ribozymes of claim 4 wherein said ribozymes are a combination of a ribozyme of SEQ ID NO:8 and a ribozyme of SEQ ID NO: 10 or 11.

7. A vector comprising DNA that encodes a ribozyme as defined in claim 1 capable of binding and cleaving Bradeion α mRNA which corresponds to DNA comprising a nucleotide sequence shown in SEQ ID NO:1.

8. A set of vectors which comprises: (i) a vector comprising DNA that encodes a ribozyme as defined in claim 1 capable of binding and cleaving Bradeion α mRNA which corresponds to DNA comprising a nucleotide sequence shown in SEQ ID NO:1; and (ii) a vector comprising DNA that encodes a ribozyme as defined in claim 1 capable of binding and cleaving Bradeion β mRNA which corresponds to DNA comprising a nucleotide sequence shown in SEQ ID NO:3, wherein each of said DNA is operably linked to a promoter.

9. A set of vectors of claim 8 wherein said promoter is a polymerase III promoter.

10. A set of vectors of claim 8 wherein said promoter is a tRNA promoter including tRNA$^{val}$ promoter or a variant thereof.

11. A set of vectors of claim 8 wherein said vectors each comprise a terminator.

12. A set of vectors of claim 8 wherein each of said vectors is adenovirus or retrovirus.

* * * * *